United States Patent [19]
Juraszyk et al.

[11] Patent Number: 5,614,535
[45] Date of Patent: Mar. 25, 1997

[54] ADHESION RECEPTOR ANTAGONISTS

[75] Inventors: Horst Juraszyk; Joachim Gante; Hanns Wurziger; Sabine Bernotat-Danielowski; Guido Melzer, all of Darmstadt, Germany

[73] Assignee: Merck Patent Gesellschaft Mit Beschrankter Haftung, Darmstadt, Germany

[21] Appl. No.: 516,937

[22] Filed: Aug. 18, 1995

[30] Foreign Application Priority Data

Aug. 19, 1994 [DE] Germany .......................... 44 29 461.1

[51] Int. Cl.$^6$ .................. A61K 31/445; A61K 31/42; C07D 263/24; C07D 413/12
[52] U.S. Cl. .................. 514/326; 514/212; 514/255; 514/364; 514/374; 540/603; 544/369; 546/208; 548/134; 548/135; 548/230
[58] Field of Search ........................... 540/603; 544/369; 546/208; 548/134, 135, 230; 514/212, 255, 326, 364, 374

[56] References Cited

U.S. PATENT DOCUMENTS

| 2,437,388 | 3/1948 | Homeyer et al. | 548/230 |
| 4,866,182 | 9/1989 | Schnettler et al. | 548/230 |
| 5,356,918 | 10/1994 | Ishihara et al. | 514/376 |

FOREIGN PATENT DOCUMENTS

| 0381033 | 8/1990 | European Pat. Off. . |
| 0462960 | 12/1991 | European Pat. Off. . |
| 0459256 | 12/1991 | European Pat. Off. . |
| 0645376 | 3/1995 | European Pat. Off. . |
| 4405633 | 11/1994 | Germany . |

OTHER PUBLICATIONS

Vajta et al. "Reversed–phase high performance liquid chromatographic separation of 14C–labeled toloxatone and tis metabolites" CA 102:5518 1984.
Born, Nature, 4832:927–929 (1962).
Smith et al., J. Biol. Chem., 265:12267–12271 (1990).

*Primary Examiner*—Ceila Chang
*Attorney, Agent, or Firm*—Millen, White, Zelano, & Branigan, P.C.

[57] ABSTRACT

Compounds of the formula I in which $R^1$ and X have the meanings herein defined, their physiologically unobjectionable salts and/or solvates inhibit the binding of fibrinogen to the corresponding receptor and can be employed for the treatment of thromboses, osteoporosis, tumoral diseases, apoplexy, cardiac infarction, inflammations, arteriosclerosis and osteolytic disorders.

20 Claims, No Drawings

ADHESION RECEPTOR ANTAGONISTS

SUMMARY OF THE INVENTION

The invention relates to oxazolidinonecarboxylic acid derivatives of the formula I

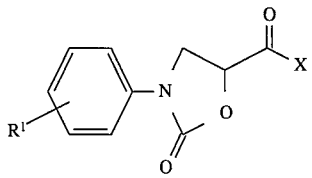

wherein $R^1$ is $NO_2$, $NR^6R^7$, CN, $CONR^6R^7$, $CSNR^6R^7$, C(=NH)SA, C(=NH)OA, C(=NH)SAr, C(=NH)NHOH, C(=)NR^6R^7, $CH_2NR^6R^7$, $CH_2NHC(=NH)NR^6R^7$, $NHC(=NH)NR^6R^7$, $CH_2NHCO$—alk—$NR^6R^7$, $CH_2NHCO$—Ph—E, $CH_2NHCO$—Ph—$CH_2NR^6R^7$, $CH_2NHCONH$—Ph—E or D, X is OH, OA, AS, AS—AS',

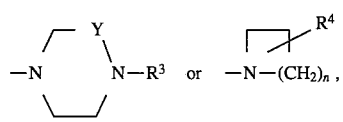

D is

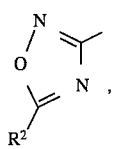

E is —CN, —C(=NH)OA, —$CSNH_2$, —C(=NH)SA or —C(=NH)$NH_2$,

Y is $CH_2$, $CHOR^5$ or C=O, $R^2$ is H, A, Ar, OH, OA, $CF_3$, $CCl_3$, $NR^6R^7$, —alk—$NR^6R^7$, —alk($CH_2Ar$)$NR^6R^7$, or

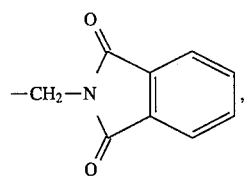

$R^3$ is —($CH_2$)$_m$—$COOR^5$, $R^4$ is —($CH_2$)$_p$—$COOR^5$ or —($CH_2$)$_q$—O—($CH_2$)$_r$—$COOR^5$,

AS or AS' is in each case, independent of the other, an amino-acid residue selected from Ala, β-Ala, Arg, Asn, Asp, Gln, Glu, Gly, Leu, Lys, Orn, Phe, Pro, Sar, Ser, Thr, Tyr, Tyr (OMe), Val, C-allyl-Gly, C-propargyl-Gly, N-benzyl-Gly, N-phenethyl-Gly, N-benzyl-β-Ala, N-methyl-β-Ala and N-phenethyl-β-Ala, it being possible for free amino or carboxyl groups also to be provided with conventional protective groups which are known per se, $R^5$, $R^6$ and $R^7$ are each, independent of one another, H or A, m is 1, 2 or 3, n is 1, 2, 3 or 4, p is 0, 1 or 2, q is 0 or 1, r is 1 or 2, A is alkyl of 1 to 6 carbon atoms, —alk— is alkylene of 1 to 6 carbon atoms, Ar is phenyl or benzyl, and Ph is phenylene, and their physiologically unobjectionable salts and/or solvates.

Compounds having a similar activity profile are known from EP-A1-0 381 033.

An object of the invention is to provide novel compounds having valuable properties, in particular those compounds which can be used for preparing medicaments.

Upon further study of the specification and appended claims, further objects and advantages of this invention will become apparent to those skilled in the art.

These objects are achieved by the invention. It has been found that the compounds of the formula I and their solvates and salts possess valuable pharmacological properties while being well tolerated. In particular, they inhibit the binding of fibrinogen, fibronectin and the von Willebrand factor to the fibrinogen receptor of blood platelets (glycoprotein IIb/IIIa), as well as the binding of these proteins and of further adhesive proteins, such as vitronectin, collagen and laminin, to the corresponding receptors on the surface of various cell types. The compounds consequently influence cell-cell and cell-matrix interactions. They prevent the development of blood-platelet thrombi in particular, and can therefore be used for the treatment of thromboses, apoplexy, cardiac infarction, inflammations and arteriosclerosis. In addition, the compounds have an effect on tumor cells, by preventing them from forming metastases. Consequently, they can also be used as antitumor agents.

There is evidence that tumor cells spreading from a solid tumor into the vasculature are carried by microthrombi, i.e., microaggregates of tumor cells and platelets. As a result, the tumor cells in the microthrombi are protected from being detected by cells of the immune system. The second step of attachment to the vessel wall seems to be facilitated by microthrombi as well. Since the formation of thrombi is mediated by fibrinogen binding to the fibrinogen receptor (glycoprotein IIb/IIIa) on activated platelets, fibrinogen-binding inhibitors are expected to be effective as antimetastatics.

Also, since fibrinogen-binding inhibitors are ligands with fibrinogen receptor on platelets, they can be used as diagnostic tools for detection and localization of thrombi in the vascular in vivo. Thus, for example, in accordance with known procedures, the fibrinogen-binding inhibitors can be labeled with a signal generating or detectable moiety whereby, once the labeled fibrinogen-binding inhibitor is bound to a fibrinogen receptor on platelets, it is possible to detect and locate thrombi.

Fibrinogen-binding inhibitors are also very effective as research tools for studying the metabolism of platelets in the different activation states or intracellular signalling mechanisms of the fibrinogen receptor. For example, as described above, fibrinogen-binding inhibitor can be labeled with a signal generating or detectable moiety. The fibrinogen-binding inhibitor-signal generating/detectable moiety conjugate can then be employed in vitro as a research tool. By binding the conjugate to fibrinogen receptors, it is possible to monitor and study the metabolism of platelets, as well as the activation states and signalling mechanisms of the fibrinogen receptors.

Furthermore, the compounds are suitable for the prophylaxis and treatment of osteolytic disorders, especially osteoporosis and restenosis following angioplasty. In addition, they have antiangiogenetic properties.

Moreover, the compounds display an antimicrobial action and can be employed in treatments and interventions in which it is necessary to prevent microbial infection. Antimicrobial activity of the compounds can be demonstrated by the procedure described by P. Valentin-Weigan et al., Infection and Immunity, 2851–2855 (1988).

The properties of the compounds can be demonstrated by methods which are described in EP-A1-0 462 960. The inhibition of the binding of fibrinogen to the fibrinogen receptor can be demonstrated by the method indicated in EP-A1-0 381 033. The inhibitory effect on blood-platelet aggregation can be demonstrated in vitro by the method of Born (Nature, 4832:927–929 (1962)). The inhibition of the interactions of $\beta_3$-integrin receptors with suitable ligands can be demonstrated by the method of J. W. Smith et al., J. Biol. Chem., 265:12267–12271 (1990).

The invention relates to compounds of the indicated formula I, to their salts and solvates, and to a process for the preparation of these compounds, characterized in that (a) a compound of the formula I is liberated from one of its functional derivatives by treatment with a solvolyzing or hydrogenolyzing agent, or in that (b) a compound of the formula II

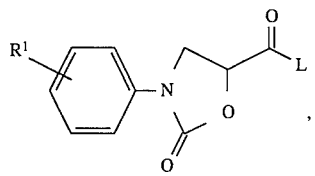

in which

R$^1$ has the meaning given and

L is Cl, Br, OH or a reactive esterified OH group or a leaving group which is readily capable of undergoing nucleophilic substitution, is reacted with a compound of the formula III

 III, in which

X' is AS, AS—AS',

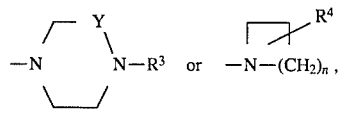

where Y, R$^3$, R$^4$ and n have the meanings given, or in that c) a radical X is converted into a different radical X by hydrolyzing an ester of the formula I or esterifying a carboxylic acid of the formula I, or in that d) a radical R$^1$ is converted into a different radical R$^1$ by catalytically hydrogenating a NO$_2$ and/or CN group, or converting a nitrile group by reaction with ammonia into a C(=NH)—NH$_2$ group, or converting a nitrile group into a thiocarbamoyl group, or converting a thiocarbamoyl group into an alkylsulfimido group, or converting a carbamoyl group into an alkylimido group, or converting a methylsulfimido group into an amidine group, or converting a nitrile group by reaction with NH$_2$OH into a C(=NH)—NHOH group, or converting a NH$_2$ group into a guanidinyl group, or converting a C(=NH)—NHOH group into an amidine group, or converting a CH$_2$NH$_2$ group into an alkanoylaminomethyl, CH$_2$NHC(=NH)NR$^6$R$^7$, CH$_2$NHCO—Ph—C(=NH)NH$_2$, CH$_2$NHCO—Ph—CH$_2$NR$^6$R$^7$ or a CH$_2$NHCONH—Ph—E group, or converting a 1,2,4-oxadiazole or 1,2,4-oxadiazolinone group into an amidine group, e) or in that a compound of the formula IV

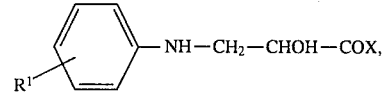 IV in which

R$^1$ and X have the given meanings, is reacted with a reactive derivative of carbonic acid, and/or in that f) a compound of the formula V

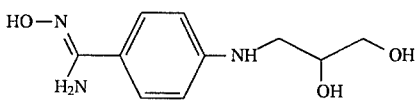 V is reacted with 2 equivalents of a reactive carbonic acid derivative and then oxidized, or in that g) a compound of the formula I is converted by treatment with an acid or a base into one of its salts.

The abbreviations given above and below for amino-acid residues are the residues of the following amino acids:

| | |
|---|---|
| Ala | alanine |
| β-Ala | β-alanine |
| Arg | arginine |
| Asn | asparagine |
| Asp | aspartic acid |
| Asp(O But) | aspartic acid β-butyl ester |
| Gln | glutamine |
| Glu | glutamic acid |
| Gly | glycine |
| Leu | leucine |
| Lys | lysine |
| Orn | ornithine |
| Phe | phenylalanine |
| Pro | proline |
| Sar | sarcosine (N-methylglycine) |
| Ser | serine |
| Thr | threonine |
| Tyr | tyrosine |
| Tyr(OMe) | 2-amino-3-p-methoxyphenylpropionic acid |
| Val | valine. |

Further abbreviations used below are:

| | |
|---|---|
| BOC | tert-butoxycarbonyl |
| CBZ | benzyloxycarbonyl |
| DCCI | dicyclohexylcarbodiimide |
| DMF | dimethylformamide |
| EDCI | N-ethyl-N'-(3-dimethylaminopropyl)-carbodiimide hydrochloride |
| Et | ethyl |
| Me | methyl |
| OMe | methyl ester |
| OEt | ethyl ester |
| TFA | trifluoroacetic acid |

Above and below, the radicals R$^1$ and X have the meanings given for the formula I. Where a compound of the formula I possesses a chiral center, it may occur in a plurality of enantiomeric forms. All of these forms and mixtures thereof, especially racemates, are included by the invention.

In the formula above and below, the group A has 1–6, preferably 1, 2, 3 or 4, carbon atoms. Specifically, A is preferably methyl, ethyl, propyl, isopropyl, butyl, isobutyl, sec-butyl or tert-butyl, and also pentyl, 1-, 2- or 3-methylbutyl, 1,1-, 1,2- or 2,2-dimethylpropyl, 1-ethylpropyl, hexyl, or 1-, 2- or 3-methylpentyl.

X is preferably —OH, —OCH$_3$, —O—CH$_2$—CH$_3$, 4-carboxypiperidino, 4-carboxyalkylpiperidino, 4-carboxyalkoxypiperidino and the corresponding alkyl ester groups of the radicals mentioned, 4-alkoxycarbonylpiperidino, 4-carboxymethylpiperazino, 4-carboxyethylpiperazino or, particularly preferably, is an amino-acid residue or a dipeptide residue which is attached to the carbonyl group via an amide bond. If X is an amino-acid residue or dipeptide residue, the following are particularly preferred: Ala, β-Ala, Gly, Arg and β-Ala-Asp, Phe, N-phenethylglycine, N-phenethyl-β-alanine or Sar.

The C-terminal amino-acid residue can in this case likewise be attached to a conventional protective group. An esterification is particularly suitable.

The group R$^1$ is preferably —NH$_2$, —C(=NH)—NH$_2$, —CH$_2$—NH$_2$, —CH$_2$—NH—CO—alk—NH$_2$, —CH$_2$—NH—CO—Ph—C(=NH)—NH$_2$, —CH$_2$—NH—CO—alk—C(=NH)—NH$_2$, —CH$_2$—NH—CO—Ph—CH$_2$—NH$_2$, NO$_2$ or CN. In addition, R$^1$ is also preferably —C(=NH)—S—A, —CSNH$_2$, —C(=NH)—NHOH or

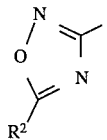

The radical Ar is unsubstituted benzyl or phenyl.

The parameters m and n are preferably 1, but also, in addition, preferably 2 or 3. The variable p is preferably 0 or 1, whereas q and r are preferably 1.

Among the compounds of the formula I, preference is given to those in which at least one of the indicated radicals, groups and/or parameters has one of the preferred meanings given. Some groups of preferred compounds are those of the formulae Ia to If, which correspond to the formula I except that in Ia R$^1$ is C(=NH)NH$_2$ and X is OH or OA;

in Ib R$^1$ is C(=NH)NH$_2$ and X is 4-carboxypiperidino, 4-carboxylalkylpiperidino or 4-carboxyalkoxypiperidino;

in Ic R$^1$ is C(=NH)NH$_2$ and X is β-Ala, Asp, Tyr, Tyr(OMe), N-phenethyl-β-Ala or Phe, and the corresponding esterified derivatives;

in Id R$^1$ is C(=NH)NH$_2$ and X is 4-alkoxycarbonylpiperidino, 4-alkoxycarbonylpiperazino, 4-alkoxycarbonylalkylpiperidino, 4-alkoxycarbonylalkoxypiperazino or 4-alkoxycarbonylalkoxypiperidino;

in Ie R$^1$ is C(=NH)NH$_2$ and X is 4-carboxypiperazino or 4-carboxyalkylpiperazino;

in If R$^1$ is C(=NH)NHOH and X is one of the radicals mentioned under Ia to Ie.

Furthermore, the invention includes all those compounds which have a NH$_2$ group within which this NH$_2$ group is provided with a protective group which is known per se.

The compounds of the formula I, and also the starting compounds for their preparation, are otherwise prepared by methods which are known per se, as described in the literature (e.g., in the standard works such as Houben-Weyl, Methoden der organischen Chemie [Methods for Organic Chemistry], Georg-Thieme-Verlag, Stuttgart; and also J. March, Adv. Org. Chem., 3rd Ed. (1985), J. Wiley & Sons), specifically under reaction conditions which are known and suitable for the stated reactions. In this context, use can also be made of variants which are known per se which are not mentioned here in more detail.

If desired, the starting compounds can also be formed in situ, such that they are not isolated from the reaction mixture but, instead, are reacted further immediately to give the compounds of the formula I.

The compounds of the formula I can be obtained by liberating them from their functional derivatives by solvolysis, in particular hydrolysis, or by hydrogenolysis.

Preferred starting compounds for the solvolysis or hydrogenolysis are those which, while otherwise corresponding to the formula I, contain corresponding protected amino and/or hydroxyl groups in place of one or more free amino and/or hydroxyl groups, preferably those which carry an amino-protective group in place of a hydrogen atom which is linked to a nitrogen atom, in particular those which carry, in place of an HN group, a group R'—N in which R' is an amino-protective group, and/or those which carry, instead of the hydrogen atom of a hydroxyl group, a hydroxy-protective group, for example those which correspond to the formula I but, instead of a —COOH group, carry a group —COOR" in which R" is a hydroxy-protective group.

It is also possible for two or more—identical or different—protected amino and/or hydroxyl groups to be present in the molecule of the starting compound. If the protective groups present are different from one another, they can in many cases be eliminated selectively.

The expression "amino-protective group" is well known and relates to groups which are suitable for protecting (for blocking) an amino group from chemical reactions but which are readily removable once the desired chemical reaction has been carried out at another site of the molecule. Typical groups of this kind are, in particular, unsubstituted or substituted acyl, aryl (e.g., 2,4-dinitrophenyl (DNP)), aralkoxymethyl (e.g., benzyloxymethyl (BOM)) or aralkyl groups (e.g., benzyl, 4-nitrobenzyl or triphenylmethyl). Since the amino-protective groups are removed after the desired reaction (or sequence of reactions), their nature and size is otherwise not critical; however, preference is given to those having 1–20, especially 1–8 carbon atoms. In connection with the present process, the expression "acyl group" should be interpreted in the broadest sense. It embraces acyl groups derived from aliphatic, araliphatic, aromatic or heterocyclic carboxylic acids or sulfonic acids and also, in particular, alkoxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or tolyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC) and 2-iodoethoxycarbonyl; aralkyloxycarbonyl such as benzyloxycarbonyl (CBZ), 4-methoxybenzyloxycarbonyl and 9-fluorenylmethoxycarbonyl (FMOC). Preferred amino-protective groups are BOC, DNP and BOM, and also CBZ, benzyl and acetyl.

The expression "hydroxy-protective group" is likewise well known and relates to groups which are suitable for protecting a hydroxyl group against chemical reactions, but which are readily removable once the desired chemical reaction has been carried out at another site of the molecule. Typical groups of this kind are the abovementioned unsubstituted or substituted aryl, aralkyl or acyl groups, and also alkyl groups. The nature and size of the hydroxy-protective groups is not critical, since after the desired chemical reaction or sequence of reactions they are removed again; preference is given to groups having 1–20, especially 1–10, carbon atoms. Examples of hydroxy-protective groups include tert-butyl, benzyl, p-nitrobenzoyl, p-toluenesulfonyl and acetyl, with particular preference being given to benzyl and acetyl.

The functional derivatives of the compounds of the formula I, which derivatives are to be used as starting compounds, can be prepared by conventional methods as described, for example, in the standard works and Patent Applications mentioned, for example by reaction of compounds which correspond to the formulae II and III but in which at least one of these compounds contains a protective group instead of a hydrogen atom.

The liberation of the compounds of the formula I from their functional derivatives is achieved—depending on the protective group used—by employing, for example, strong acids, advantageously using trifluoroacetic or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary.

Suitable inert solvents are preferably organic, for example carboxylic, acids such as acetic acid, ethers such as tetrahydrofuran (THF) or dioxane, amides such as dimethylformamide (DMF), halogenated hydrocarbons such as dichloromethane, and also alcohols such as methanol, ethanol or isopropanol, and water. Also suitable are mixtures of the abovementioned solvents. Trifluoroacetic acid is preferably used in excess without the addition of a further solvent, perchloric acid in the form of mixture of acetic acid and 70% perchloric acid in a ratio of 9:1. The reaction temperatures for the cleavage are advantageously between about 0° and about 50°; it is preferably carried out at between 15° and 30° (room temperature).

The BOC group may, for example, preferably be eliminated using 40% trifluoroacetic acid in dichloromethane or with from about 3 to 5N HCl in dioxane at 15°–60°, and the FMOC group removed using an approximately 5–20% solution of dimethylamine, diethylamine or piperidine in DMF at 15°–50°. Elimination of the DNP group is also achieved, for example, with an approximately 3–10% solution of 2-mercaptoethanol in DMF/water at 15°–30°.

Protective groups which can be removed by hydrogenolysis (e.g., BOM, CBZ or benzyl) may, for example, be eliminated by treatment with hydrogen in the presence of a catalyst (e.g., a noble metal catalyst such as palladium, advantageously on a support such as charcoal). In this case suitable solvents are those indicated above, particular examples being alcohols such as methanol or ethanol, or amides such as DMF. The hydrogenolysis is generally carried out at temperatures of between 0° and 100° and at pressures of between 1 and 200 bar, preferably 20°–30° and 1–10 bar. Hydrogenolysis of the CBZ group is readily achieved, for example, over 5–10% Pd-C in methanol at 20°–30°.

It is also possible, for example, to perform a hydrogenolytic conversion of a 1,2,4-oxadiazolin-5-on-3-yl or a 5-alkyl-1,2,4-oxadiazol-3-yl group into amidine group by catalytic hydrogenation.

Compounds of the formula I can also be obtained, preferably, by reaction of an oxazolidinone of the formula II with a compound of the formula III. In this case use is advantageously made of the methods which are known per se of nucleophilic substitution and/or of the N-alkylation of amines or the reactions for amide formation.

The leaving group L in the formula II is preferably Cl, Br or OH, or a group which can be derived therefrom, for example the trifluoromethanesulfonyloxy, toluenesulfonyloxy or methanesulfonyloxy group.

The reaction is preferably carried out in the presence of an additional base, for example an alkali metal or alkaline-earth metal hydroxide or carbonate, such as sodium hydroxide, potassium hydroxide or calcium hydroxide, sodium carbonate, potassium carbonate or calcium carbonate, in an inert solvent, for example a halogenated hydrocarbon such as dichloromethane, an ether such as THF or dioxane, an amide such as DMF or dimethylacetamide, or a nitrile such as acetonitrile, at temperatures of between about –10° and 200°, preferably between 0° and 120°. The addition of an iodide such as potassium iodide may favor the progress of the reaction.

The starting compounds of the formula II are in general known or can be prepared in an analogy to known compounds. Their preparation is described, for example, in DE 37 23 797 (EP 300 272). They can be prepared, for example, by reacting an appropriately substituted aniline with allyl chloride, subsequently converting the double bond into a diol, reacting this diol with a reactive derivative of carbonic acid, for example phosgene, N-N-carbonyldiimidazole, a dialkyl carbonate or diphosgene, oxidizing the product to 5-oxazolidinonecarboxylic acid and, if desired, carrying out further activation by derivatizing the acid group, In a compound of the formula II it is possible to convert a radical L into a different radical L by, for example, reacting an OH group (Y=OH) with $SOCl_2$, $SOBr_2$, methanesulfonylchloride or p-toluenesulfonyl chloride.

The compounds of the formula III are, in general, known and commercially available The reaction of the oxazolidinones of the formula II with the compounds of the formula III is carried out in a manner known per se, preferably in a protic or aprotic polar inert solvent at temperatures of between 20° and the boiling point of the solvent. The reaction times are from 10 min to 24 h, preferably from 2 h to 10 h.

Suitable solvents include, in particular, alcohols such as methanol, ethanol, isopropanol, n-butanol and tert-butanol; ethers such as diethyl ether, diisopropyl ether, tetrahydrofuran (THF) and dioxane; glycol ethers such as ethylene glycol monomethyl and monoethyl ether (methyl glycol or ethyl glycol), and ethylene glycol dimethyl ether (diglyme); ketones such as acetone and butanone; nitriles such as acetonitrile; nitro compounds such as nitromethane and nitrobenzene; esters such as ethyl acetate and hexamethylphosphoric triamide; sulfoxides such as dimethyl sulfoxide (DMSO); chlorinated hydrocarbons such as dichloromethane, chloroform, trichloroethylene, 1,2-dichloroethane and carbon tetrachloride; and hydrocarbons such as benzene, toluene and xylene. Also suitable are mixtures of these solvents with one another. N-methylpyrrolidone is particularly suitable.

Derivatives having a free primary or secondary amino group are advantageously converted into a protected form. Suitable protective groups are those mentioned above.

It is also possible to obtain a compound of the formula I by converting a radical X into a different radical X. For example, a free acid group (X=OH) can be esterified (X=OA) or linked by a peptide bond to an amino acid or a dipeptide. Furthermore, it is also possible, for example, to convert an acid into an amide.

In addition, it is possible to obtain a compound of the formula I by converting a radical $R^1$ in a compound of the formula I into a different radical $R^1$.

In particular, cyano groups can be reduced to aminomethyl groups or converted into amidino groups, benzyl groups can be removed by hydrogenolysis, aminomethyl groups can be converted into guanidinomethyl groups, or nitrile groups can be converted into thiocarbamoyl groups.

A reduction of cyano groups to aminomethyl groups is carried out advantageously by catalytic hydrogenation, for example over Raney-Nickel at temperatures between 0° and 100°, preferably 10° and 30°, and at pressures between 1 and 200 bar, preferably at atmospheric pressure, in an inert solvent, for example a lower alcohol such as methanol or ethanol, advantageously in the presence of ammonia. If the operation is carried out, for example, at about 20° and 1 bar, then benzyl ester groups or N-benzyl groups present in the starting material are retained. If it is desired to cleave these by hydrogenolysis, then use is advantageously made of a noble metal catalyst, preferably Pd/charcoal, in which case it is possible to add to the solution an acid such as acetic acid, and also water.

In order to prepare compounds of the formula I in which $R^1$ is a guanidinophenyl group, a corresponding aminophenyl compound can be treated with an amidinating agent. A preferred amidinating agent is 1-amidino-3,5-dimethylpyrazole, which is employed in particular in the form of its nitrate. The operation is advantageously carried out with the addition of a base, such as triethylamine or ethyldiisopropylamine, in an inert solvent or solvent mixture, for example water/dioxane, at temperatures of between 0° and 120°, preferably between 60° and 120°.

In order to prepare an amidine of the formula I, ammonia can be added on to a nitrile of the formula I. The addition is preferably accomplished over two or more stages in a manner known per se by a) converting the nitrile with $H_2S$ into a thioamide which is converted with an alkylating agent, for example $CH_3I$, into the corresponding S-alkyl-imidothio ester, which in turn is reacted with $NH_3$ to give the amidine, b) converting the nitrile with an alcohol, for example ethanol, in the presence of HCl into the corresponding imido ester and treating the latter with ammonia, or c) reacting the nitrile with lithium bis(trimethylsilyl)amide and then hydrolyzing the product.

Analogously, the corresponding N-hydroxy amidines of the formula I are obtainable from the nitriles by working in accordance with a) or b) but using hydroxylamine instead of ammonia.

Furthermore, N-hydroxyamidines can be converted, by reaction with aliphatic carbonyl chlorides, into 1,2,4-oxadiazoles or 1,2,4-oxadiazolinones, which can then be converted, by catalytic hydrogenation over, for example, Raney-Ni, Pd/C or $PtO_2$, preferably in MeOH, dioxane, glacial acetic acid, glacial acetic acid/acetic anhydride or DMF, into amidines.

Furthermore, a compound of the formula I can be obtained by reacting a compound of the formula IV with a reactive derivative of carbonic acid. Reactive derivatives of carbonic acid may, for example, be those mentioned above, with particular preference being given to phosgene and diphosgene and to N,N-carbonyldiimidazole. Further suitable carbonic acid derivatives are, in particular, dialkyl carbonates such as diethyl carbonate, and also alkyl chloroformates such as ethyl chloroformate. It is preferred for the carbonic acid derivative, which is advantageously employed in excess, also to act as the solvent or suspension medium. It is also possible, however, for one of the solvents indicated to be present, provided it is inert in this reaction. Furthermore, the addition of a base is advisable, especially an alkali metal alcoholate such as potassium tert-butylate. The reaction is advantageously carried out at a temperature of between 0° and 150°, preferably between 70° and 120°.

The starting compounds of the formula IV are, in general, novel. They are obtainable, for example, by reacting a ring-substituted aniline with an α-hydroxy-β-halocarboxylic acid.

It is possible, moreover, to obtain a compound of the formula I by reacting a diol of the formula V with an excess of a reactive carbonic acid derivative, a reaction which is preferably carried out under the abovementioned conditions. While the carbonic acid derivatives are commercially available, the compounds of the formula V can be obtained, for example, by reacting allyl chloride with p-aminobenzonitrile, converting the double bond into a dihydroxy grouping, and reacting the resulting compound with hydroxylamine.

A base of the formula I can be converted with an acid into the corresponding acid addition salt. Acids suitable for this reaction are in particular those which give physiologically unobjectionable salts. For instance, it is possible to use inorganic acids, for example sulfuric acid, nitric acid, hydrohalic acids such as hydrochloric acid or hydrobromic acid, phosphoric acids such as orthophosphoric acid, sulfamic acid, and also organic acids, especially aliphatic, alicyclic, araliphatic, aromatic or heterocyclic mono- or polybasic carboxylic, sulfonic or sulfuric acids, for example formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and lauryl sulfuric acid.

The free bases of the formula I may, if desired, be liberated from their salts by treatment with strong bases such as sodium hydroxide or potassium hydroxide, sodium carbonate or potassium carbonate.

It is also possible to convert carboxylic acids of the formula I, by reaction with corresponding bases, into their metal or ammonium salts, for example their sodium, potassium or calcium salts.

The compounds of the formula I may contain one or more chiral centers and may therefore be present in racemic or in optically active form. Racemates which are obtained can be separated by methods which are known per se, mechanically or chemically, into the enantiomers.

Preferably, diastereomers are formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid.

Also advantageous is an enantiomeric resolution using a column packed with an optically active resolving agent (e.g., dinitrobenzoylphenylglycine); a suitable eluent is, for example, a hexane/isopropanol/acetonitrile mixture.

It is of course also possible to obtain optically active compounds of the formula I in accordance with the methods described above by using starting compounds (e.g., those of the formula II) which are already optically active.

The novel compounds of the formula I and their physiologically unobjectionable salts may be used for producing pharmaceutical preparations by bringing them into a suitable dosage form, together with at least one excipient or auxiliary and, if desired, together with one or more further active compounds. The formulations thus obtained can be employed as medicaments in human or veterinary medicine. Suitable excipients are organic or inorganic substances which are suitable for enteral (e.g., oral or rectal) or parenteral administration, or for administration in the form of an inhalation spray, and which do not react with the novel compounds, examples of the excipients being water, vegetable oils, benzyl alcohols, polyethylene glycols, glycerol triacetate and other fatty acid glycerides, gelatin, soya bean lecithin, carbohydrates such ,as lactose or starch, magnesium stearate, talc and cellulose. For oral use, tablets, coated tablets, capsules, syrups, juices or drops are used in particular; of special interest are film-coated tablets and capsules having gastric juice-resistant coatings or capsule casings. Suppositories are employed for rectal use, while for parenteral administration use is made of solutions, preferably oily or aqueous solutions, and also suspensions, emulsions or implants.

For administration as inhalation spray, sprays can be used which contain the active compound either dissolved or suspended in a propellant gas mixture. In this case the active compound is advantageously used in micronized form, with it being possible for one or more additional, physiologically compatible solvents to be present, for example ethanol. Inhalation solutions can be administered with the aid of conventional inhalers. The novel compounds may also be lyophilized and the resulting lyophilizates used, for example, to produce preparations for injection. The formulations indicated can be sterilized and/or contain auxiliaries such as preservatives, stabilizers and/or wetting agents, emulsifiers, salts for influencing the osmotic pressure, buffer substances, colorants and/or aroma substances. They may if desired also contain one or more further active compounds, for example one or more vitamins.

The substances according to the invention are generally administered in analogy to other known, commercially available pharmaceuticals, but especially in analogy to the compounds described in EP-A-459 256, preferably in doses of about 5 mg–1 g, in particular 50–500 mg, per dosage unit. The daily dose is preferably about 0.1–20 mg/kg, in particular 1–10 mg/kg, of body weight. The specific dose for each particular patient depends, however, on a wide variety of factors, for example on the activity of the specific compound employed, on the age, body weight, general condition of health, sex, on the diet, on the time and route of administration, on the speed of excretion, on the combination of medicaments employed and on the severity of the particular disease to which the therapy is applied. Oral administration is preferred.

Suitable preparations for using the compounds as antimicrobial agents are, for example, injection vials, ampoules, solutions and capsules. Carriers, excipients and further additives are mentioned in Examples A–H. The amount of the inventive compound in the antimicrobial agents is preferably about 0.05–500 mg/dosage unit.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosure of all applications, patents and publications, cited above and below, and of corresponding German application P 44 29 461.1, are hereby incorporated by reference.

EXAMPLES

Above and below, all temperatures are indicated in °C. In the examples below, "customary workup" means: water is added if necessary, the pH is adjusted, depending on the constitution of the end product, to between 2 and 8, extraction takes place with ethyl acetate or dichloromethane, the phases are separated, the organic phase is dried over sodium sulfate and concentrated by evaporation, and the residue is purified by chromatography on silica gel and/or crystallization. Where molecular masses are indicated, then conventional mass-spectroscopic values are designated by "M" and fast atom bombardment (FAB) values are designated by "M+1".

Example 1

1 g of 4-(2-oxo-5-hydroxymethyloxazolidin-3-yl)benzonitrile [obtainable according to EP 300 272] dissolved in 12 ml of acetonitrile is added at 16° to a solution of 3.6 g of Na dihydrogen phosphate dihydrate, 3.9 g of Na metaperiodate and 36 mg of $RuCl_3$ in 23 ml of water/2.3 ml of dichloromethane. The reaction mixture is stirred at room temperature for 12 h, filtered and given the customary workup. Concentration by evaporation to dryness in vacuo gives 3-(4-cyanophenyl)-2-oxo-5-oxazolidinecarboxylic acid, m.p. 204°.

Example 2

27.9 g of 3-(4-cyanophenyl)-2-oxo-5-oxazolidine carboxylic acid [obtainable according to Example 1] and 26.4 g of hydroxylammonium chloride are boiled for 5 h in a mixture of 750 ml of methanol and 30 ml of water in the presence of 53.4 g of sodium carbonate. The precipitate formed is filtered off with suction, washed with methanol and dried. Treatment with hydrochloric acid gives 3-[4-(amino(hydroxylimino)methyl)phenyl]-2-oxo-5-oxazolidinecarboxylic acid, hydrochloride, m.p. 205°–208°.

Example 3

13.9 g of 3-[4-(amino(hydroxylimino)methyl)phenyl]-2-oxo-5-oxazolidinecarboxylic acid [obtainable according to Example 2] are dissolved in 210 ml of glacial acetic acid, 11.3 g of trichloromethyl chloroformate are added, and the mixture is boiled for 3 h. It is then cooled to room temperature and given the customary workup. 3-[4-(5-Oxo-1,2,4-oxadiazolin-3-yl)phehyl]-2-oxo-5-oxazolidinecarboxylic acid is obtained, m.p. 250°–253°.

Example 4

3.03 g of N-methylmorpholine are added to a solution of 2.91 g of 3-[4-(5-oxo-1,2,4-oxadiazolin-3-yl)phenyl]-2-oxo-5-oxazolidinecarboxylic acid [obtainable according to Example 3], 2.77 g of tert-butyl piperidine-4-carboxylate, 2.02 g of 1-hydroxybenzotriazole and 2.86 g of N-(3-dimethylaminopropyl)-N'-ethylcarbodiimide hydrochloride in 20 ml of DMF, and the mixture is stirred at room temperature for 5 h. 200 ml of water are subsequently added dropwise with intensive stirring, the crystalline precipitate formed is separated off and taken up in 90 ml of dichloromethane, and the mixture is dried over $Na_2SO_4$. The solution is concentrated in vacuo, and the resulting oil is triturated with diethyl ether to give tert-butyl 1-{3-[4-(5-oxo-1,2,4-oxadiazolin-3-yl)phenyl]-2-oxo-5-oxazolidinylcarbonyl}piperidine-4carboxylate, m.p. 171°–175°.

The following are obtained analogously by reacting 3-[4-(5-oxo-1,2,4-oxadiazolin-3-yl)phenyl]-2-oxo-5-oxazolidinecarboxylic acid with tert-butyl 2-(piperid-4-yl)acetate: tert-butyl 2-{1-[3-(4-(5-oxo-1,2,4-oxadiazolin-3-yl)phenyl)-2-oxo-5-oxazolidinylcarbonyl]piperid-4-yl} acetate;

with ethyl 2-(piperid-4-yl)acetate: ethyl 2-{1-[3-(4-(5-oxo-1,2,4-oxadiazolin-3-yl)phenyl)-2-oxo-5-oxazolidinylcarbonyl]piperid-4-yl} acetate; mp. 178°–181°;

with tert-butyl 2-(piperid-4-yl-oxy)acetate: tert-butyl 2-{1-[3 -(4 -(5-oxo-1,2,4-oxadiazolin-3-yl) phenyl)-2-oxo-5-oxazolidinylcarbonyl ]piperid-4-yl-oxy} acetate; mp. 180°–181°;

with tert-butyl 2 -(piperid-3-yl-oxy)acetate: tert-butyl 2-{1-[3-(4-(5-oxo-1,2,4-oxadiazolin-3-yl)phenyl)-2-oxo-5-oxazolidinylcarbonyl ]piperid-3-yl-oxy} acetate; mp. 92°–95°;

with tert-butyl-2-(2-oxo-piperazino) acetate: tert-butyl-2-{4-[3-(4-(5-oxo-1,2,4-oxadiazolin-3-yl)phenyl)-2-oxo-5-oxazolidinylcarbonyl ]2-oxopiperazino} acetate; mp. 155°–157°;

with tert-butyl (2R)-2-aminopropionate (H-Ala-OBut): tert-butyl (2R)-2-{3-[4-(5-oxo-1,2,4-oxadiazolin-3-yl) phenyl]-2-oxo-5-oxazolidinylcarbonylamino} propionate; mp. 105°–107°;

with methyl (2R)-2-aminopropionate (H-Ala-OMe): methyl (2R)-2-{3-[4-(5-oxo-1,2,4-oxadiazolin-3-yl)phenyl]-2-oxo-5-oxazolidinylcarbonylamino}propionate; mp. 199°–201°;

with di-tert-butyl (2R)-2-aminosuccinate (H-Asp(OBut)-OBut): di-tert-butyl (2R)-2-{3-[4-(5-oxo-1,2,4-oxadiazolin-3-yl)phenyl]-2-oxo-5-oxazolidinylcarbonylamino}succinate; mp. 175°–176°;

with tert-butyl 3-aminopropionate (H-βAla-OBut): tert-butyl 3-{3-[4-(5-oxo-1,2,4-oxadiazolin-3-yl)phenyl]-2-oxo-5-oxazolidinylcarbonylamino}propionate, m.p. 143°–146°;

with methyl 3-aminopropionate (H-βAla-OMe): methyl 3-{3-[4-(5-oxo-1,2,4-oxadiazolin-3-yl)phenyl]-2-oxo-5-oxazolidinylcarbonylamino}propionate, m.p. 230°–232°;

with tert-butyl (2R)-2-amino-3-(4-hydroxyphenyl)propionate (H-Tyr-OBut): tert-butyl (2R)-2-{3-[4-(5-oxo-1,2,4-oxadiazolin-3-yl)phenyl]-2-oxo-5-oxazolidinylcarbonylamino}-3-(4-hydroxyphenyl)propionate;

with tert-butyl (2R)-2-amino-3-(4-methoxyphenyl)propionate (H-Tyr-(OMe)-OBut): tert-butyl (2R)-2-{3-[4-(5-oxo-1,2,4-oxadiazolin-3-yl)phenyl]-2-oxo-5-oxazolidinylcarbonylamino}-3-(4-methoxyphenyl)propionate;

with tert-butyl 3-N-phenethylaminopropionate: tert-butyl 3-{3-[4-(5-oxo-1,2,4-oxadiazolin-3-yl)phenyl]-2-oxo-5-oxazolidinylcarbonyl-(N-phenethyl)amino} propionate;

with benzyl 2-piperazino acetate: benzyl 2-{1-[3-(4-(5-oxo-1,2,4-oxadiazolin-3-yl)phenyl)-2-oxo-5-oxazolidinylcarbonyl]piperazin-4-yl}acetate, m.p. 165°–170°;

with benzyl 3-piperazino propionate: benzyl 3-{1-[3-(4-(5-oxo-1,2,4-oxadiazolin-3-yl)phenyl)-2-oxo-5-oxazolidinylcarbonyl]piperazin-4-yl}propionate, m.p. 150°–153°.

Example 5

1.37 g of tert-butyl 1-{3-[4-(5-oxo-1,2,4-oxadiazolin-3-yl)phenyl]-2-oxo-5-oxazolidinylcarbonyl}piperidine-4-carboxylate are dissolved in 50 ml of methanol and hydrogenated over Raney nickel. The reaction mixture is, subsequently filtered and the filtrate is concentrated in vacuo. The product obtained is treated with 20 ml of ethyl acetate, with heating, and the product, after cooling, is filtered off with suction. Tert-butyl 1-[3-(4-amidinophenyl)-2-oxo-5-oxazolidinylcarbonyl}piperid-4-yl-carboxylate is obtained, m.p. 160°.

The following are obtained analogously by reductive cleavage of the 5-oxo-1,2,4-oxadiazoline group, from tert-butyl 2-{1-[3-(4-(5-oxo-1,2,4-oxadiazolin-3-yl)phenyl)-2-oxo-5-oxazolidinylcarbonyl]piperid-4-yl}acetate: tert-butyl 2-{1-[3-(4-amidinophenyl)-2-oxo-5-oxazolidinylcarbonyl]piperid-4-yl}acetate;

from ethyl 2-{1-[3-(4-(5-oxo-1,2,4-oxadiazolin-3-yl)phenyl)-2-oxo-5-oxazolidinylcarbonyl]piperid-4-yl}acetate: ethyl 2-{1-[3-(4-amidinophenyl)-2-oxo-5-oxazolidinylcarbonyl]piperid-4-yl}acetate, m.p. 210°–211° from tert-butyl 2-{1-[3-(4-(5-oxo-1,2,4-oxadiazolin-3-yl)phenyl)-2-oxo-5-oxazolidinylcarbonyl]piperid-4-yl-oxy}acetate: tert-butyl 2-{1-[3-(4-amidinophenyl)-2-oxo-5-oxazolidinylcarbonyl]piperid-4-yl-oxy}acetate, m.p. 100°;

from tert-butyl 2-{1-[3-(4-(5-oxo-1,2,4-oxadiazolin-3-yl)phenyl)-2-oxo-5-oxazolidinylcarbonyl]piperid-3-yl-oxy}acetate: tert-butyl 2-{1-[3-(4-amidinophenyl)-2-oxo-5-oxazolidinylcarbonyl]piperid-3-yl-oxy}acetate, m.p. 139°–144°;

from tert-butyl 2-{4-[3-(4-(5-oxo-1,2,4-oxadiazolin-3-yl)phenyl)-2-oxo-5-oxazolidinylcarbonyl]-2-oxo-piperazino}acetate: tert-butyl 2-{4-[3-(4-amidinophenyl)-2-oxo-5-oxazolidinylcarbonyl]-2-oxo-piperazino}acetate, m.p. 165°–167°;

from tert-butyl (2R)-2-{3-[4-(5-oxo-1,2,4-oxadiazolin-3-yl)phenyl]-2-oxo-5-oxazolidinylcarbonylamino}propionate: tert-butyl (2R)-2-[3-(4-amidinophenyl)-2-oxo-5-oxazolidinylcarbonylamino]propionate, m.p. 173°–175°;

from methyl (2R)-2-{3-[4-(5-oxo-1,2,4-oxadiazolin-3-yl)phenyl]-2-oxo-5-oxazolidinylcarbonylamino}propionate: methyl (2R)-2-[3-(4-amidinophenyl)-2-oxo-5-oxazolidinylcarbonylamino]propionate, acetate, m.p. 190°–192°;

from di-tert-butyl (2R)-2-{3-[4-(5-oxo-1,2,4-oxadiazolin-3-yl)phenyl]-2-oxo-5-oxazolidinylcarbonylamino}succinate: di-tert-butyl (2R)-2-[3-(4-amidinophenyl)-2-oxo-5-oxazolidinylcarbonylamino]succinate, acetate, m.p. 242°;

from tert-butyl 3-{3-[4-(5-oxo-1,2,4-oxadiazolin-3-yl)phenyl]-2-oxo-5-oxazolidinylcarbonylamino}propionate: tert-butyl 3-[3-(4-amidinophenyl)-2-oxo-5-oxazolidinylcarbonylamino]propionate, m.p. 164°–167°;

from methyl 3-{3-[4-(5-oxo-1,2,4-oxadiazolin-3-yl)phenyl]-2-oxo-5-oxazolidinylcarbonylamino}propionate: methyl 3-[3-(4-amidinophenyl)-2-oxo-5-oxazolidinylcarbonylamino]propionate, acetate, m.p. 207°–209°;

from tert-butyl (2R)-2-{3-[4-(5-oxo-1,2,4-oxadiazolin-3-yl)phenyl]-2-oxo-5-oxazolidinylcarbonylamino}-3-(4-hydroxyphenyl)propionate: tert-butyl (2R)-2-[3-(4-amidinophenyl)-2-oxo-5-oxazolidinylcarbonylamino]-3-(4-hydroxyphenyl)propionate;

from tert-butyl (2R)-2-{3-[4-(5-oxo-1,2,4-oxadiazolin-3-yl)phenyl]-2-oxo-5-oxazolidinylcarbonylamino}-3-(4-methoxyphenyl)propionate: tert-butyl (2R)-2-[3-(4-amidinophenyl)-2-oxo-5-oxazolidinylcarbonylamino]-3-(4-methoxyphenyl)propionate;

from tert-butyl 3-{3-[4-(5-oxo-1,2,4-oxadiazolin-3-yl)phenyl)-2-oxo-5-oxazolidinylcarbonyl-(N-phenethyl)amino}propionate: tert-butyl 3-[3-(4-amidinophenyl)-2-oxo-5-oxazolidinylcarbonyl-(N-phenethyl)amino]propionate;

from benzyl 2-{1-[3-(4-(5-oxo-1,2,4-oxadiazolin-3-yl)phenyl)-2-oxo-5-oxazolidinylcarbonyl]piperazin-4-yl} acetate: benzyl 2-{1-[3-(4-amidinophenyl)-2-oxo-5-oxazolidinylcarbonyl]piperazin-4-yl}acetate;
from benzyl 3-{1-[3-(4-(5-oxo-1,2,4-oxadiazolin-3-yl)phenyl)-2-oxo-5-oxazolidinylcarbonyl]piperazin-4-yl}propionate: benzyl 3-{1-[3-(4-amidinophenyl)-2-oxo-5-oxazolidinylcarbonyl]piperazin-4-yl}propionate;

Example 6

0.41 g of tert-butyl 1-[3-(4-amidinophenyl)-2-oxo-5-oxazolidinylcarbonyl}piperidin-4-yl-carboxylate is stirred in 40 ml of ethereal HCl solution at room temperature for 2 h. The precipitate formed is filtered off with suction and washed with 20 ml of ether. The product is then treated with 5 ml of acetonitrile at 60° for 10 min, the mixture is cooled to room temperature, and the product is filtered off with suction and washed with a little acetonitrile. 1-[3-(4-amidinophenyl)-2-oxo-5-oxazolidinylcarbonyl]piperidine-4-carboxylic acid, hydrochloride, m.p. 184° (decomposition), is obtained.

The following are obtained analogously by hydrolysis of the corresponding esters,
from tert-butyl 2-{1-[3-(4-amidinophenyl)-2-oxo-5-oxazolidinylcarbonyl ]piperid-4-yl}acetate: 2-{1-[3-(4-amidinophenyl)-2-oxo-5-oxazolidinylcarbonyl]piperid-4-yl} acetic acid, hydrochloride;
from tert-butyl 2-{1-[3-(4-amidinophenyl)-2-oxo-5-oxazolidinylcarbonyl]piperid-4-yl-oxy} acetate: 2-{1-[3-(4-amidinophenyl)-2-oxo-5-oxazolidinylcarbonyl]piperid-4-yl-oxy}acetic acid, hydrochloride; m.p. 170°–175° (decomposition);
from tert-butyl 2-{1-[3-(4-amidinophenyl)-2-oxo-5-oxazolidinylcarbonyl]piperid-3-yl -oxy} acetate: 2-{1-[3-(4-amidinophenyl)-2-oxo-5-oxazolidinylcarbonyl]piperid-3-yl-oxy} acetic acid, hydrochloride; m.p. 127°–129°;
from tert-butyl 2-{4-[3-(4-amidinophenyl)-2-oxo-5-oxazolidinylcarbonyl]-2-oxo-piperazino} acetate: 2-{4-[3-(4-amidinophenyl)-2-oxo-5-oxazolidinylcarbonyl]-2-oxo-piperazino} acetic acid, hydrochloride, m.p. 68°–70°;
from tert-butyl (2R)-2-[3-(4-amidinophenyl)-2-oxo-5-oxazolidinylcarbonylamino]propionate; (2R)-2-[3-(4-amidinophenyl)-2-oxo-5-oxazolidinylcarbonylamino]propionic acid, hydrochloride, m.p. 190°–204°;
from di-tert-butyl (2R)-2-[3-(4-amidinophenyl)-2-oxo-5-oxazolidinylcarbonylamino]succinate; (2R)-2-[3-(4-amidinophenyl)-2-oxo-5-oxazolidinylcarbonylamino]succinic acid, hydrochloride, m.p. 308°–310° (decomposition);
from tert-butyl 3-[3-(4-amidinophenyl)-2-oxo-5-oxazolidinylcarbonylamino]propionate: 3-[3-(4-amidinophenyl)-2-oxo-5-oxazolidinylcarbonylamino]propionic acid, hydrochloride, m.p. 243°–244° (decomposition);
from tert-butyl (2R)-2-[3-(4-amidinophenyl)-2-oxo-5-oxazolidinylcarbonylamino]-3-(4-hydroxyphenyl)propionate: (2R)-2-[3-(4-amidinophenyl)-2-oxo-5-oxazolidinylcarbonylamino]-3-(4-hydroxyphenyl)propionate, hydrochloride;
from tert-butyl (2R)-2-[3-(4-amidinophenyl)-2-oxo-5-oxazolidinylcarbonylamino]-3-(4-methoxyphenyl)propionate: (2R)-2-[3-(4-amidinophenyl)-2-oxo-5-oxazolidinylcarbonylamino]-3-(4-methoxyphenyl)propionic acid, hydrochloride;
from tert-butyl (2R)-2-[3-(4-amidinophenyl)-2-oxo-5-oxazolidinylcarbonyl-(N-phenethyl)amino]propionate: (2R)-2-[3-(4-amidinophenyl)-2-oxo-5-oxazolidinylcarbonyl-(N-phenethyl)-amino]propionic acid, hydrochloride.

Example 7

1.0 g of benzyl 2-{1-[3-(4-amidinophenyl)-2-oxo-5-oxazolidinylcarbonyl]-piperazin-4-yl} acetate is catalytically hydrogenated over Pd/charcoal, in a mixture of 100 ml of methanol and 50 ml of DMF, until the end of hydrogen uptake. The reaction mixture subsequently filtered and given the customary workup. Trituration of the crude product with ether and drying give 2-{1-[3-(4-amidinophenyl)-2-oxo-5-oxazolidinylcarbonyl]-piperazin-4-yl} acetic acid, m.p. 220°–225° (decomposition).

The following is obtained analogously from benzyl 3-{1-[3-(4-amidinophenyl)-2-oxo-5-oxazolidinylcarbonyl]piperazin-4-yl} propionate: 3-{1-[3-(4-amidinophenyl)-2-oxo-5-oxazolidinylcarbonyl]-piperazin-4-yl}propionic acid, m.p. 255°–258° (decomposition).

Example 8

In analogy to Example 4, reaction of phenylalanine tert-butyl ester and 3-(4-cyanophenyl)-2-oxo-5-oxazolidinecarboxylic acid [obtainable according to Example 1] gives tert-butyl (2R)-2-[3-(4-cyanophenyl)-2-oxo-5-oxazolidinylcarbonylamino]-3-phenylpropionate, m.p. 72°.

The following are obtained analogously by reacting 3-(4-cyanophenyl)-2-oxo-5-oxazolidinecarboxylic acid with benzyl piperidine-4-carboxylate:
benzyl 1-[3-(4-cyanophenyl)-2-oxo-5-oxazolidinylcarbonyl]piperidine-4-carboxylate, FAB (M+1): 434;
with tert-butyl 2-(4-piperidyloxy)acetate: tert-butyl 2-{1-[3-(4-cyanophenyl)-2-oxo-5-oxazolidinylcarbonyl]-4-piperidinyloxy}acetate, m.p. 126°–127°.

Example 9

2.3 g of 3-(4-cyanophenyl)-2-oxo-5-oxazolidinecarbonyl chloride (m.p. 148°–150°; obtainable from the acid by reaction with oxalyl chloride] are reacted with one equivalent of benzyl 1-piperazinyl acetate, hydrochloride, in 100 ml of dichloromethane in the presence of 5 ml of triethylamine at room temperature. Customary workup gives benzyl 2-{1-[3-(4-cyanophenyl)-2-oxo-5-oxazolidinyl carbonyl]-4piperazinyl}acetate, m.p. 131°–132°.

Example 10

2.6 g of tert-butyl (2R)-2-[3-(4-cyanophenyl)-2-oxo-5-oxazolidinylcarbonylamino]-3-phenylpropionate [obtainable according to Example 8] are dissolved in a solvent mixture consisting of 30 ml of pyridine and 5 ml of triethylamine and the mixture is stirred for 1.5 h with ice cooling, with $H_2S$ gas being passed in continuously during this phase. The reaction mixture is subsequently stirred at room temperature for 24 h. Concentration by evaporation and customary workup give tert-butyl (2R)-2-[3-(4-thiocarbamoylphenyl)-2-oxo-5-oxazolidinylcarbonylamino]-3-phenylpropionate, m.p. 185°–186°.

The following are obtained analogously:
from benzyl 1-[3-(4-cyanophenyl)-2-oxo-5-oxazolidinylcarbonyl]-piperidine-4-carboxylate: benzyl 1-[3-(4-thiocarbamoylphenyl)-2-oxo-5-oxazolidinylcarbonyl]-piperidine-4-carboxylate, m.p. 167°–169°;
from tert-butyl 2-{1-[3-(4-cyanophenyl)-2-oxo-5-oxazolidinylcarbonyl]-4-piperidyloxy}acetate: tert-butyl 2-{1-[3-(4-thiocarbamoylphenyl)-2-oxo-5-oxazolidinylcarbonyl]-4-piperidinyloxy}acetate, m.p. 190°–191°;

from benzyl 2-{1-[3-(4-cyanophenyl)-2-oxo-5-oxazolidinylcarbonyl]-4-piperazinyl}acetate: benzyl 2-{1-[3-(4-thiocarbamoylphenyl)-2-oxo-5-oxazolidinylcarbonyl]-4-piperazinyl}acetate.

Example 11

0.92 g of tert-butyl (2R)-2-[3-(4-thiocarbamoylphenyl)-2-oxo-5-oxazolidinylcarbonylamino]-3-phenylpropionate [obtainable according to Example 10] is dissolved in 15 ml of acetone, and 1.75 ml of methyl iodide are added. The solution is stirred at room temperature for 2 h and given the customary workup. tert-Butyl, (2R)-2-[3-(4-imino(methylthio)methylphenyl)-2-oxo-5-oxazolidinylcarbonylamino]-3-phenylpropionate, hydroiodide, is obtained, m.p. 140°.

The following are obtained analogously:
from benzyl 1-[3-(4-thiocarbamoylphenyl)-2-oxo-5-oxazolidinylcarbonyl]-piperidine-4-carboxylate: benzyl 1-[3-(4-imino-(methylthio)methylphenyl)-2-oxo-5-oxazolidinylcarbonyl]piperidine-4-carboxylate, hydroiodide, m.p. 86°–91°;
from tert-butyl 2-{1-[3-(4-thiocarbamoylphenyl)-2-oxo-5-oxazolidinylcarbonyl]-4-piperidyloxy}acetate: tert-butyl 2-{1-[3-(4-imino(methylthio)methylphenyl)-2-oxo-5-oxazolidinylcarbonyl]-4-piperidyloxy}acetate, m.p. 157°;
from benzyl 2-{1-[3-(4-thiocarbamoylphenyl)-2-oxo-5-oxazolidinylcarbonyl]-4-piperazinyl}acetate: benzyl 2-{1-[3-(4-imino(methylthio)methylphenyl)-2-oxo-5-oxazolidinylcarbonyl]-4piperazinyl}acetate.

Example 12

0.45 g of tert-butyl (2R)-2-[3-(4-imino(methylthio)methylphenyl)-2-oxo-5-oxazolidinylcarbonylamino]-3-phenylpropionate obtainable according to Example 11] is suspended in 5 ml of methanol, 0.47 g of ammonium acetate is added, and the mixture is stirred at room temperature for 24 h. 10 ml of ether are then added to the reaction mixture, and the precipitate formed is separated off. Concentration by evaporation, customary workup and treatment with glacial acetic acid give tert-butyl (2R)-2-[3-(4-amidinophenyl)-2-oxo-5-oxazolidinylcarbonylamino]-3-phenylpropionate, acetate, m.p. 191°–192°.

The following are obtained analogously:
from benzyl 1-[3-(4-imino-(methylthio)methylphenyl)-2-oxo-5-oxazolidinylcarbonyl]piperidine-4-carboxylate:
benzyl 1-[3-(4-amidinophenyl)-2-oxo-5-oxazolidinylcarbonyl]piperidine-4-carboxylate, acetate, m.p. 197°–199°;
from tert-butyl 2-{1-[3-(4-imino-(methylthio)methylphenyl)-2-oxo-5-oxazolidinylcarbonyl]piperidyloxy}acetate:
tert-butyl 2-{1-[3-(4-amidinophenyl)-2-oxo-5-oxazolidinylcarbonyl]-4-piperidyloxy)acetate, acetate, m.p. 127°–126°;
from benzyl 2-{1-[3-(4-imino-(methylthio)methylphenyl)-2-oxo-5-oxazolidinylcarbonyl]-4-piperazinyl}acetate:
benzyl 2-{1-[3-(4-amidinophenyl)-2-oxo-5-oxazolidinylcarbonyl]-4-piperazinyl}acetate, acetate.

Example 13

0.25 g of tert-butyl (2R)-2-[3-(4-amidinophenyl)-2-oxo-5-oxazolidinylcarbonylamino)-3phenylpropionate [obtainable according to Example 12]is stirred in 10 ml of trifluoroacetic acid at room temperature until hydrolysis is complete. The reaction mixture is subsequently concentrated and the residue is washed repeatedly with toluene. Treatment with ethyl acetate gives (2R)-2-[3-(4-amidinophenyl)-2-oxo-5-oxazolidinylcarbonylamino]-3-phenylpropionic acid, trifluoroacetate, FAB (M+1): 397.

The following are obtained analogously by hydrolysis of the corresponding esters from Example 12:
1-[3-(4-amidinophenyl)-2-oxo-5-oxazolidinylcarbonyl]piperidine-4-carboxylic acid, trifluoroacetate;
2-{1-[3-(4-amidinophenyl)-2-oxo-5-oxazolidinylcarbonyl]-4-piperidyloxy}acetic acid, trifluoroacetate;
2-{1-[3-(4-amidinophenyl)-2-oxo-5-oxazolidinylcarbonyl]-4-piperazinyl}acetic acid, trifluoroacetate.

Example 14

23.2 g of 3-(4-cyanophenyl)-2-oxo-5-oxazolidinecarboxylic acid [obtainable according to Example 1] are hydrogenated, together with 33.0 g of di-tert-butyl dicarbonate in 1000 ml of methanol and 110 ml of 1N sodium hydroxide solution, over Pd/charcoal until the uptake of hydrogen comes to a standstill. The solution is then concentrated in vacuo. Customary workup gives 3-(4-tert-butoxycarbonylaminomethylphenyl)-2-oxo-5-oxazolidinecarboxylic acid, m.p. 166°.

Example 15

In analogy to Example 4, reaction of benzyl 3-(1-piperazinyl)propionate and 3-(4-tert-butoxycarbonylaminomethylphenyl)-2-oxo-5-oxazolidinecarboxylic acid gives benzyl 3-{1-[3-(4-tert-butoxycarbonylaminomethylphenyl)-2-oxo-5-oxazolidinylcarbonyl]-4-piperazinyl}propionate, m.p. 128°–130°.

The following are obtained analogously by reacting 3-(4-tert-butoxycarbonylaminomethylphenyl)-2-oxo-5-oxazolidinecarboxylic acid
with benzyl piperidine-4-carboxylate: benzyl 1-[3-(4-tert-butoxycarbonylaminomethylphenyl)-2-oxo-5-oxazolidinylcarbonyl]piperidine-4-carboxylate;
with tert-butyl 2-(4-piperidyloxy)acetate: tert-butyl 2-{1-[3-(4-tert-butoxycarbonylaminomethylphenyl)-2-oxo-5-oxazolidinylcarbonyl]-4piperidyloxy}acetate, m.p. 115°–119°;
with benzyl 2-(4-piperazinyl)acetate: benzyl 2-{1-[3-(4-tert-butoxycarbonylaminomethylphenyl)-2-oxo-5-oxazolidinylcarbonyl]-4piperazinyl}acetate, m.p. 121°;
with tert-butyl 4-piperidinecarboxylate: tert-butyl 1-[3-(4-tert-butoxycarbonylaminomethylphenyl)-2-oxo-5-oxazolidinylcarbonyl]-4-piperidinecarboxylate, m.p. 63.5°;
with tert-butyl (2R)-2-amino-3-phenylpropionate: tert-butyl (2R)-2-[3-(4-tert-butoxycarbonylaminomethylphenyl)-2-oxo-5-oxazolidinylcarbonylamino]-3-phenylpropionate, m.p. 68°–69°.

Example 16

1.5 g of benzyl 3-{1-[3-(4-tert-butoxycarbonylaminomethylphenyl)-2-oxo-5-oxazolidinylcarbonyl]-4-piperazinyl}propionate are hydrogenated in 50 ml of DMF over 5% Pd/charcoal. After customary workup, the crude product is dissolved in a solvent mixture consisting of dichloromethane/methanol/glacial acetic acid (70:30:2) and chromatographed over silica gel. Trituration of the product with ether gives 3-{1-[3-(4-tert-butoxycarbonylaminomethylphenyl)-2-oxo-5-oxazolidinylcarbonyl]-4-piperazinyl}propionic acid, m.p. 76°–78°.

Example 17

0.53 g of tert-butyl 2-{1-[3-(4-tert-butoxycarbonylaminomethylphenyl)-2-oxo-5-oxazolidinylcarbonyl]-4-piperidyloxy}acetate is stirred in 10 ml of trifluoroacetic acid at room temperature. After customary workup, the crude product is triturated with ether and dried. 2-{1-[3-(4-aminomethylphenyl)-2-oxo-5-oxazolidinylcarbonyl]-4-piperidyloxy}acetic acid, trifluoroacetate, is obtained, FAB (M+1): 378.

The following are obtained analogously:
from tert-butyl (2R)-2-[3-(4-tert-butoxycarbonylaminomethylphenyl)-2-oxo-5-oxazolidinylcarbonyl]-3-phenylpropionate: (2R)-2-[3-(4-aminomethylphenyl)-2-oxo-5-oxazolidinylcarbonyl]-3-phenylpropionic acid, trifluoroacetate, m.p. 178°–185°.

Example 18

0.5 g of tert-butyl 1-[3-(4-tert-butoxycarbonylaminomethylphenyl)-2-oxo-5-oxazolidinylcarbonyl]piperidine-4-carboxylate is stirred in 10 ml of trifluoroacetic acid at room temperature. The solution is concentrated in vacuo. The crude product is subsequently treated with ethereal hydrochloric acid, filtered off with suction and dried. 1-[3-(4-aminomethylphenyl)-2-oxo-5-oxazolidinylcarbonylpiperidine-4-carboxylic acid, hydrochloride, is obtained, m.p. 256°–258° (decomposition).

Example 19

0.43 g of 3-{1-[3-(4-tert-butoxycarbonylaminomethylphenyl)-2-oxo-5-oxazolidinylcarbonyl]-4-piperazinyl}propionic acid, acetate, is stirred in 30 ml of ethereal HCl solution at room temperature. The precipitate formed is filtered off with suction, washed with a little ether and dried. 3-{1-[3-(4-aminomethylphenyl)-2-oxo-5-oxazolidinylcarbonyl]-4-piperazinyl}propionic acid, dihydrochloride, is obtained, m.p. 184°–186°.

Example 20

0.74 g of benzyl 2-{1-[3-(4-tert-butoxycarbonylaminomethylphenyl)-2-oxo-5-oxazolidinylcarbonyl]-4-piperazinyl}acetate is stirred in 30 ml of HCl solution in ethyl acetate at room temperature. The precipitate formed is filtered off through suction, washed with a little ethyl acetate and dried. Benzyl 2-{1-[3-(4-aminomethylphenyl)-2-oxo-5-oxazolidinylcarbonyl]-4-piperazinyl}acetate, dihydrochloride, is obtained, m.p. 224°–226°.

Example 21

0.6 g of benzyl 2-{1-[3-(4-aminomethylphenyl)-2-oxo-5-oxazolidinylcarbonyl]-4-piperazinyl}acetate, dihydrochloride, is hydrogenated over Pd/charcoal, in a mixture of 30 ml of methanol, 5 ml of water and 5 ml of glacial acetic acid. The reaction mixture is filtered and the filtrate is concentrated in vacuo. Trituration of the crude product with ethyl acetate gives 2-{1-[3-(4-aminomethylphenyl)-2-oxo-5-oxazolidinylcarbonyl]-4-piperazinyl}acetic acid, dihydrochloride, m.p. 91° (decomposition).

Example 22

5.4 g of 3-(4-aminomethylphenyl)-2-oxo-5-oxazolidinecarboxylic acid are suspended in 70 ml of THF. 35 ml of 1N NaOH are added dropwise with stirring. Subsequently, a solution of 6.6 g of 4-cyanobenzoyl chloride in 60 ml of THF is added dropwise. The pH of the solution is maintained at between 9 and 10.5 by addition of 1N NaOH. After reaction has taken place, the mixture is acidified at a pH of 1 with 2N HCl. The solvent is removed and the residue is filtered off with suction and washed with water. 3-[4-(4-cyanobenzamidomethyl)phenyl]-2-oxo-5-oxazolidinecarboxylic acid is obtained, m.p. 234°.

The following is obtained analogously by reacting 3-(4-aminomethylphenyl)-2-oxo-5-oxazolidinecarboxylic acid with p-chlorocarbonylaminobenzonitrile: 3-{4-[3-(4-cyanophenyl)-ureidomethyl]phenyl}-2-oxo-5-oxazolidinecarboxylic acid.

Example 23

In analogy to Example 10, reaction of 3-[4-(4-cyanobenzamidomethyl)phenyl]-2-oxo-5-oxazolidinylcarboxylic acid with hydrogen sulfide gives 3-[4-(4-thiocarbamoylbenzamidomethyl)phenyl]-2-oxo-5-oxazolidinecarboxylic acid, m.p. 105°–110°.

The following compound is obtained analogously by reacting 3-{4-[3-(4-cyanophenyl)ureidomethyl]phenyl}-2-oxo-5-oxazolidinylcarboxylic acid with hydrogen sulfide: 3-{4-[3-(4-thiocarbamoylphenyl)ureidomethyl]phenyl}-2-oxo-5-oxazolidinylcarboxylic acid.

Example 24

In analogy to Example 11, reaction of 3-[4-(4-thiocarbamoylbenzamidomethyl)phenyl]-2-oxo-5-oxazolidinylcarboxylic acid with methyl iodide gives 3-[4-(4-imino(methylthio)methylbenzamidomethyl)phenyl]-2-oxo-5-oxazolidinecarboxylic acid, hydroiodide, m.p. 209°.

The following compound is obtained analogously by reacting 3-{4-[3-(4-thiocarbamoyl-phenyl)ureidomethyl]phenyl}-2-oxo-5-oxazolidine-carboxylic acid with methyl iodide: benzyl 3-{4-[3-(4-imino(methylthio)methylphenyl)-ureidomethyl]phenyl}-2-oxo-5-oxazolidinecarboxylate.

Example 25

In analogy to Example 12, reaction of 3-[4-(4-imino(methylthio)methylbenzamidomethyl)phenyl]-2-oxo-5 -oxazolidinylcarboxylic acid with ammonium acetate gives 3-[4-(4-amidinobenzamidomethyl)phenyl]-2-oxo-5-oxazolidinecarboxylic acid, acetate, m.p. 294°.

The following compound is obtained analogously by reacting benzyl 3-{4-[3-(4-imino(methylthio)methylphenyl)ureidomethyl]phenyl}-2-oxo-5-oxazolidinecarboxylate with ammonium acetate: 3-{4-[3-(4-amidinophenyl)ureidomethyl]phenyl}-2-oxo-5-oxazolidinecarboxylic acid, acetate.

Example 26

In analogy to Example 21, elimination of the benzyl ester group starting from benzyl 3-[4-(4-amidinobenzamidomethyl)phenyl]-2-oxo-5-oxazolidinecarboxylate gives 3-[4-(4- amidinobenzamidomethyl)phenyl]-2-oxo-5-oxazolidinecarboxylic acid.

The following compound is obtained analogously by eliminating the benzyl ester group starting from benzyl 3-{4-[3-(4-amidinophenyl)ureidomethyl]phenyl}-2-oxo-5-oxazolidinylcarboxylate: 3-{4-[3-(4-amidinophenyl)ureidomethyl]phenyl}-2-oxo-5-oxazolidinylcarboxylic acid.

Example 27

3.36 g of 3-(4-tert-butoxycarbonylaminomethylphenyl)-2-oxo-5-oxazolidinecarboxylic acid [obtainable according to Example 14; m.p. 166°] are stirred at room temperature for 1 h in a mixture of 30 ml of ether and 30 ml of dioxane, which has been saturated beforehand with HCl gas. The precipitate is then filtered off with suction and washed with ether. 3-(4-Aminomethylphenyl)-2-oxo-5-oxazolidinecarboxylic acid is obtained, m.p. 211°–212°.

Example 28

0.22 g of tert-butyl (2R)-2-[3-(4-cyanophenyl)-2-oxo-5-oxazolidinylcarbonylamino-3-phenylpropionate [obtainable according to Example 8] are stirred at room temperature for 1 hour in 5 ml of trifluoroacetic acid. The solution is then concentrated in vacuo and the residue is triturated with ether. (2R)-2-[3-(4 -cyanophenyl)-2-oxo-5-oxazolidinylcarbonylamino]-3-phenylpropionic acid, trifluoroacetate, is obtained.

Example 29

0.26 g of 3-[4-amino(hydroxyimino)methylphenyl]-2-oxo-5-oxazolidinecarboxylic acid [obtainable according to Example 2] are boiled for 2 h in a mixture of 10 ml of glacial acetic acid and 10 ml of acetic anhydride. The reaction solution is concentrated in vacuo and the residue is crystallized from ether. 3-[4-(5-methyl-1,2,4-oxadiazol-3-yl)phenyl]-2-oxo-5-oxazolidinecarboxylic acid is obtained, m.p. 215°–218°.

Example 30

1.06 g of 3-[4-amino(hydroxyimino)methylphenyl]-2-oxo-5-oxazolidinecarboxylic acid [obtainable according to Example 2] and 1.47 g of chloroacetyl chloride are boiled for 2 h in 20 ml of glacial acetic acid. The reaction solution is concentrated in vacuo and the residue is crystallized from ether. 3-[4-(5-Chloromethyl-1,2,4-oxadiazol-3-yl)phenyl]-2-oxo-5-oxazolidinecarboxylic acid is obtained, m.p. 178°–181°.

Example 31

1.32 g of 3-[4-amino(hydroxyimino)methylphenyl]-2-oxo-5-oxazolidinecarboxylic acid [obtainable according to Example 2] and 4.44 g of N-(chlorocarbonylmethyl)phthalimide are boiled for 2 h in 20 ml of glacial acetic acid. The reaction solution is cooled to room temperature and the precipitate is filtered off with suction, washed with ether and glacial acetic acid and recrystallized from ethanol. 3-[4-(5-phthalimidomethyl-1,2,4-oxadiazol-3-yl)phenyl]-2-oxo-5-oxazolidinecarboxylic acid is obtained, m.p. 130°–135°.

Example 32

15 g of 3-[4-amino(hydroxyimino)methylphenyl]-2-oxo-5-oxazolidinecarboxylic acid [obtainable according to Example 2] are hydrogenated over Pd/charcoal, in 370 ml of glacial acetic acid with the addition of 13 ml of acetic anhydride, until the hydrogen uptake comes to a standstill. The catalyst is removed by filtration and the filtrate is discarded. The solid residue is then treated with 100 ml of 1N HCl solution and 200 ml of concentrated HCl solution and filtered. The hydrochloric acid-containing filtrate is concentrated in vacuo and the crystalline residue which separates out in the course of this operation is filtered off. Washing with little water and drying give 3-(4-amidinophenyl)-2-oxo-5-oxazolidinecarboxylic acid, hydrochloride, m.p. 253°–254°.

Example 33

0.87 g of benzyl 1-[3-(4-cyanophenyl)-2-oxo-5-oxazolidinylcarbonyl]piperidine-4-carboxylate [obtainable according to Example 8], 0.43 g of hydroxylammonium chloride and 0.89 g of sodium carbonate are boiled for 3 h in 12.5 ml of methanol with the addition of 0.5 ml of water. The reaction solution is subsequently given the customary workup. A mixture is obtained of benzyl 1-{3-[4-amino(hydroxyimino)methylphenyl]-2-oxo-5-oxazolidinylcarbonyl}piperidine-4-carboxylate, FAB (M+1): 467 and methyl 1-{3-[4-amino(hydroxyimino)methylphenyl]-2-oxo-5-oxazolidinylcarbonyl}piperidine-4-carboxylate, FAB (M+1): 391. The two substances are separated by means of column chromatography (silica gel: dichloromethane/methanol 93:7).

Example 34

1.12 g of methyl 3-{3-[4-(5-oxo-1,2,4-oxadiazolin-3-yl)phenyl]-2-oxo-5-oxazolidinylcarbonylamino}propionate [obtainable according to Example 4] are stirred at room temperature for 3 h in 13.5 ml of water and 30 ml of methanol with the addition of 1.35 g of potassium carbonate. The reaction solution is then given the customary workup. 3-{3-[4-(5-Oxo-1,2,4-oxadiazolin-3-yl)phenyl]-2-oxo-5-oxazolidinylcarbonylamino)propionic acid is obtained, m.p. 221°–223°.

The examples which follow relate to pharmaceutical formulations:

Example A: Injection vials

A solution of 100 g of an active compound of the formula I and 5 g of disodium hydrogen phosphate in 3 l of double-distilled water is adjusted to a pH of 6.5 with 2N hydrochloric acid, subjected to sterile filtration, dispensed into injection vials and lyophilized under sterile conditions, and the injection vials are sealed in a sterile manner. Each injection vial contains 5 mg of active compound.

Example B: Suppositories

A mixture of 20 g of an active compound of the formula I with 100 g of soya bean lecithin and 1400 g of cocoa butter is melted, poured into moulds and allowed to cool. Each suppository contains 20 mg of active compound.

Example C: Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The pH is adjusted to 6.8, and the solution is made up to 1 l and sterilized by irradiation. This solution can be used in the form of eye drops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is pressed to give tablets in a customary manner such that each tablet contains 10 mg of active compound.

Example F: Coated tablets

Tablets are pressed analogously to Example E and are then coated in a customary manner with a coating of sucrose, potato starch, talc, tragacanth and colorant.

Example G: Capsules 2 kg of active compound of the formula I are used to fill hard gelatin capsules in a customary manner, so that each capsule contains 20 mg of the active compound

Example H: Ampoules

A solution of 1 kg of active compound of the formula I in 60 l of double-distilled water is subjected to sterile filtration, dispensed into ampoules and lyophilized under sterile conditions, and the ampoules are sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An oxazolidinonecarboxylic acid compound of formula I

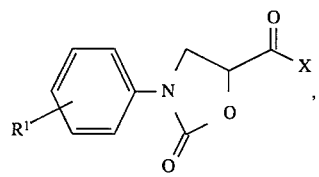

wherein $R^1$ is $NO_2$, $NR^6R^7$, CN, $CONR^6R^7$, $CSNR^6R^7$, C(=NH)SA, C(=NH)OA, C(=NH)SAr, C(=NH)NHOH, C(=NH)$NR^6R^7$, $CH_2NR^6R^7$, $CH_2NHC(=NH)NR^6R^7$, NHC(=NH)$NR^6R^7$, $CH_2NHCO$—alk—$NR^6R^7$, $CH_2NHCO$—Ph—E, $CH_2NHCO$—Ph—$CH_2NR^6R^7$, $CH_2NHCONH$—Ph—E or D;

X is OH, OA, AS, AS—AS',

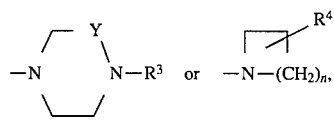

wherein when X is AS or AS—AS', X is joined to the carbonyl group by an α-amino or β-amino group;

D is

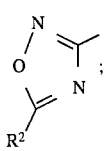

E is —CN, —C(=NH)OA, —$CSNH_2$, —C(=NH)SA or —C(=NH)$NH_2$;

Y is $CH_2$, $CHOR^5$ or C=O;

$R^2$ is H, A, Ar, OH, OA, $CF_3$, $CCl_3$, $NR^6R^7$, —alk—$NR^6R^7$, —alk—$(CH_2Ar)NR^6R^7$ or

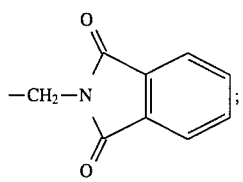

$R^3$ is —$(CH_2)_m$—$COOR^5$;

$R^4$ is —$(CH_2)_p$—$COOR^5$ or —$(CH_2)_q$—O—$(CH_2)_r$—$COOR^5$;

AS and AS' are in each case independently, an amino-acid residue selected from Ala, β-Ala, Arg, Asn, Asp, Gln, Glu, Gly, Leu, Lys, Orn, Phe, Pro, Sar, Ser, Thr, Tyr, Tyr (OMe), Val, C-allyl-Gly, C-propargyl-Gly, N-benzyl-Gly, N-phenethyl-Gly, N-benzyl-β-Ala, N-methyl-β-Ala and N-phenethyl-β-Ala, wherein free amino and carboxyl groups are optionally protected with protective groups;

$R^5$, $R^6$ and $R^7$ are each independently H or A;

m is 1, 2 or 3;

n is 1, 2, 3 or 4;

p is 0, 1 or 2;

q is 0 or 1;

r is 1 or 2;

A is alkyl of 1 to 6 carbon atoms;

—alk— is alkylene of 1 to 6 carbon atoms;

Ar is phenyl or benzyl; and

Ph is phenylene; or a physiologically acceptable salt thereof.

2. A compound according to claim 1, wherein said compound is an enantiomer or diastereomer.

3. A compound according to claim 1, wherein free amino, amidino or guanidino groups are protected in part or in whole by amino-protective groups.

4. A compound according to claim 1, wherein said compound is:

(a) 2-[1-(3-(4-amidinophenyl)-2-oxo-5-oxazolidinecarbonyl)piperidin-4-yl-oxy]acetic acid or a physiologically acceptable salt thereof;

(b) (2R)-2-[3-(4-amidinophenyl)-2-oxo-5-oxazolidinylcarbonylamino]succinic acid or a physiologically acceptable salt thereof;

(c) 3-[3-(4-amidinophenyl)-2-oxo-5-oxazolidinylcarbonylamino]propionic acid or a physiologically acceptable salt thereof;

(d) tert-butyl 1-[3-(4-amidinophenyl)-2-oxo-5-oxazolidinylcarbonyl]piperidine-4-carboxylate;

(e) di-tert-butyl (2R)-2-[3-(4-amidinophenyl)-2-oxo-5-oxazolidinylcarbonylamino]succinate;

(f) tert-butyl 1-[3-(4-(5-oxo-1,2,4-oxadiazolin-3-yl)phenyl)-2-oxo-5-oxazolidinyl]piperidine-4-carboxylate;

(g) 3-[4-(amino(hydroxylimino)methyl)phenyl]-2-oxo-5-oxazolidinecarboxylic acid or a physiologically acceptable salt thereof;

(h) (2R)-2-[3-(4-cyanophenyl)-2-oxo-5-oxazolidinylcarbonylamino]-3-phenylpropionic acid or a physiologically acceptable salt thereof;

(i) 3-[3-(4-(5-oxo-1,2,4-oxazolidin-3-yl)phenyl)-2-oxo-5-oxazolidinylcarbonylamino]propionic acid or a physiologically acceptable salt thereof.

5. A process for preparation of a compound according to claim 1, wherein a) a compound of the formula I is liberated from one of its functional derivatives by treatment with a solvolyzing or hydrogenolyzing agent; or b) a compound of the formula II

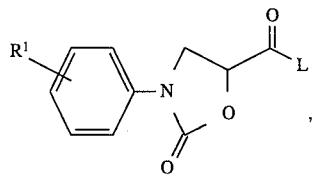

in which $R^1$ has the meaning given, and

L is Cl, Br, OA, OH or a reactive esterified OH group or a leaving group which is readily capable of undergoing nucleophilic substitution, is reacted with a compound of the formula III

H—X'  III, in which

X' is AS, AS—AS',

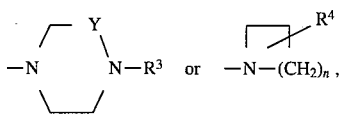

where Y, $R^3$, $R^4$ and n have the meanings given; or c) a radical X is converted into a different radical X by hydrolyzing an ester of the formula I, or esterifying a carboxylic acid of the formula I; or d) a radical $R^1$ is converted into a different radical $R^1$ by catalytically hydrogenating a $NO_2$ and/or CN group, or converting a nitrile group by reaction with ammonia into a C(=NH)—$NH_2$ group, or converting a nitrile group into a thiocarbamoyl group, or converting a thiocarbamoyl group into an alkylsulfimido group, or converting a carbamoyl group into an alkylimido group, or converting a methylsulfimido group into an amidine group, or converting a nitrile group by reaction with $NH_2OH$ into a C(=NH)—NHOH group, or converting a $NH_2$ group into a guanidinyl group, or converting a C(=NH)—NHOH group into an amidine group, or converting a $CH_2NH_2$ group into an alkanoylaminomethyl, $CH_2NHC$(=NH)$NR^6R^7$, $CH_2NHCO$—Ph—C(=NH)$NR^6R^7$, $CH_2NHCO$—Ph—$CH_2NR^6R^7$ or a $CH_2NHCONH$—Ph—E group, or converting a 1,2,4-oxadiazole or 1,2,4-oxadiazolinone group into an amidine group; or e) a compound of the formula IV

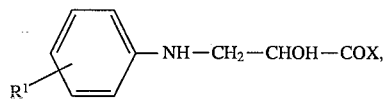

in which $R^1$ and X have the given meanings, is reacted with a reactive derivative of carbonic acid; and/or f) a compound of the formula V

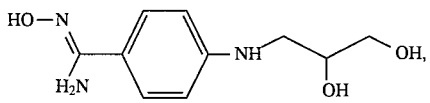

is reacted with 2 equivalents of a reactive carbonic acid derivative and then oxidized; or g) a compound of the formula I is converted by treatment with an acid or a base into one of its salts.

6. A process for preparation of a pharmaceutical formulation, comprising bringing together into a form suitable for administration a compound according to claim 1 and at least one solid, liquid or semiliquid excipient or auxiliary.

7. A pharmaceutical composition comprising at least one compound according to claim 1 and a physiologically acceptable carrier.

8. A compound according to claim 1, wherein $R^1$ is C(=NH)$NH_2$.

9. A compound according to claim 1, wherein $R^1$ is C(=NH)NH$_2$ and X is OH or OA.

10. A compound according to claim 1, wherein $R^1$ is C(=NH)NH$_2$ and X is 4-carboxypiperidino, 4-carboxyalkylpiperidino or 4-carboxyalkoxypiperidino.

11. A compound according to claim 1, wherein $R^1$ is C(=NH)NH$_2$ and X is β-Ala, Asp, Tyr, Tyr(OMe), N-phenethyl-β-Ala or Phe, or a corresponding esterified derivative.

12. A compound according to claim 1, wherein $R^1$ is C(=NH)NH$_2$ and X is 4-alkoxycarbonylpiperidino, 4-alkoxycarbonylpiperazino, 4-alkoxycarbonylalkylpiperidino, 4-alkoxycarbonylalkoxypiperazino or 4-alkoxycarbonylalkoxypiperidino.

13. A compound according to claim 1, wherein $R^1$ is C(=NH)NH$_2$ and X is 4-carboxypiperazino or 4-carboxyalkylpiperazino.

14. A compound according to claim 1, wherein $R^1$ is C(=NH)NH$_2$ and X is OH, OA, 4-carboxypiperidino, 4-carboxyalkylpiperidino, 4-carboxyalkoxypiperidino, β-Ala, Asp, Tyr, Tyr(OMe), N-phenethyl-β-Ala, Phe, 4-alkoxycarbonylpiperidino, 4-alkoxycarbonylpiperazino, 4-alkoxycarbonylalkylpiperidino, 4-alkoxycarbonylalkoxypiperazino, 4-alkoxycarbonylalkoxypiperidino, 4-carboxypiperazino or 4-carboxyalkylpiperazino.

15. A compound according to claim 1, wherein X is —OH, —OCH$_3$, —O—CH$_2$—CH$_3$, 4-carboxypiperidino, 4-carboxyalkylpiperidino, 4-carboxyalkoxypiperidino, 4-alkoxycarbonylpiperidino, 4-carboxymethylpiperazino or 4-carboxyethylpiperazino.

16. A compound according to claim 1, wherein X is Ala, β-Ala, Gly, Arg, β-Ala-Asp, Phe, N-phenethyl-Gly, N-phenethyl-β-Ala or Sar.

17. A compound according to claim 1, wherein $R^1$ is —NH$_2$, —C(=NH)—NH$_2$, —CH$_2$NH$_2$, —CH$_2$—NH—CO—alk—NH$_2$, —CH$_2$—NH—CO—Ph—C(=NH)—NH$_2$, —CH$_2$—NH—CO—alk—C(=NH)—NH$_2$, —CH$_2$—NH—CO—Ph—CH$_2$—NH$_2$, NO$_2$, CN, —C(=NH)—S—A, —CSNH$_2$, —C(=NH)—NHOH or

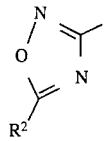

18. A composition according to claim 7, wherein the amount of said compound is 50–500 mg.

19. A method of preventing the development of blood-platelet thrombi in a patient comprising administering a compound according to claim 1.

20. A method according to claim 19, wherein the amount of said compound is 1–10 mg/kg of body weight.

* * * * *